United States Patent [19]

Buzby, Jr. et al.

[11] Patent Number: 4,644,081
[45] Date of Patent: Feb. 17, 1987

[54] PROCESS FOR THE ASYMMETRIC SYNTHESIS OF CHIRAL INDOLINE-2-CARBOXYLIC ACIDS

[75] Inventors: George C. Buzby, Jr., Blue Bell; Michael W. Winkley; Ronald J. McCaully, both of Malvern, all of Pa.

[73] Assignee: American Home Products Corporation, New York, N.Y.

[21] Appl. No.: 829,662

[22] Filed: Feb. 14, 1986

Related U.S. Application Data

[63] Continuation of Ser. No. 700,379, Feb. 11, 1985.

[51] Int. Cl.$^4$ .......................................... C07C 101/447
[52] U.S. Cl. .................................................. 562/456
[58] Field of Search ....................................... 562/456

[56] References Cited

U.S. PATENT DOCUMENTS

| | | | |
|---|---|---|---|
| 2,705,726 | 4/1955 | Archer | 562/456 |
| 3,397,211 | 8/1968 | Summit | 562/456 |
| 4,060,626 | 11/1977 | Hrstka et al. | 424/274 |

FOREIGN PATENT DOCUMENTS

2085880 5/1982 United Kingdom ............... 562/456

OTHER PUBLICATIONS

Houlihan, ed., The Chemistry of Heterocyclic Compounds, vol. 25, part 1, pp. 396–399 (Wiley Interscience, New York 1972).
Hudson, C. B. and Robertson, A. V., Australian Journal of Chemistry 20, 1935–41 (1967).
Stanton et al., Journal of Medicinal Chemistry, 26, 1267–77, 1268 (1983).
Corey et al., Journal of the American Chemical Society, 2476–2488, at 2480 (1970).
Vincent et al., Tetrahedron Letters, vol. 23, No. 16, pp. 1677–1680 at 1678 (Apr./May 1982).
Hepburn et al., Chem. Abstracts, 82: 3698n (1975).

*Primary Examiner*—James H. Reamer
*Attorney, Agent, or Firm*—Arthur G. Seifert

[57] ABSTRACT

Disclosed herein is a process for producing an asymmetric indoline-2-carboxylic acid of the structural Formula:

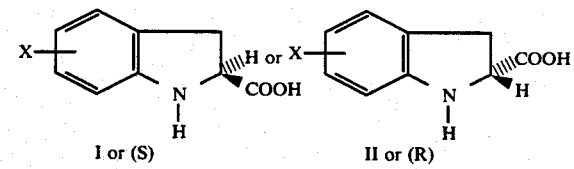

I or (S)   II or (R)

wherein X is hydrogen, bromine, chlorine, $C_{1-4}$ alkyl or $C_{1-4}$ alkoxy, which comprises:

(a) assymetrically reducing an o-nitrophenylpyruvic acid III by contacting the acid III with a reducing complex formed from (R)-proline or (S)-proline, respectively, and sodium borohydride in an inert solvent to form, respectively, an (S) or (R)-α-hydroxy-2-nitrobenzenepropanoic acid IV;

(b) reacting, respectively, said (S) or (R)-α-hydroxy-2-nitrobenzenepropanoic acid III with a Vilsmeier chlorinating reagent in which the chlorinating agent thereof is selected from a group consisting of thionyl chloride, oxalyl chloride, phosphorus oxychloride, phosphorus pentachloride and sulfuryl chloride and the amide thereof is selected from a group consisting of dimethylformamide, diethylformamide, dimethylacetamide and diethylacetamide, said reaction being run at temperatures of at least 20° C., in order to obtain, respectively, and (R) or (S)-α-chloro-2-nitrobenzenepropanoic acid IV;

(c) reducing the nitro group of said (R) or (S)-α-chloro-2-nitrobenzenepropanoic acid (V) to an amino group; and (d) cyclizing the resulting (R) or (S)-α-chloro-2-aminobenzenepropanoic acid in aqueous base.

3 Claims, No Drawings

PROCESS FOR THE ASYMMETRIC SYNTHESIS OF CHIRAL INDOLINE-2-CARBOXYLIC ACIDS

This is a continuation of application Ser. No. 700,379, filed Feb. 11, 1985.

The invention relates to a novel process for the asymmetric synthesis of indoline-2-carboxylic acids of the structural Formulas I and II, wherein X can be hydrogen, chlorine, bromine, $C_{1-4}$ alkyl or $C_{1-4}$ alkoxy.

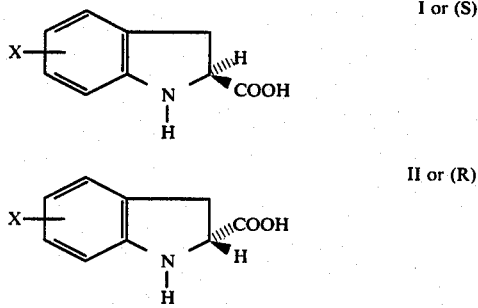

The overall process is illustrated by the following diagram for the preparation of (S)-indoline-2-carboxylic acid:

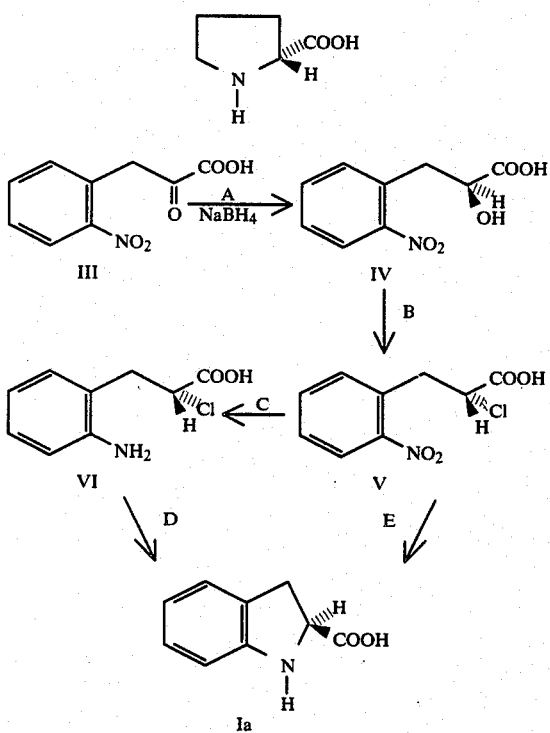

Step A in this process is also novel and patent protection is sought for it as well as for the overall process. In addition the intermediate (R) or (S)-α-chloro-2-aminobenzenepropanoic acids (V) are novel and patent protection is likewise sought for these compounds.

BACKGROUND OF THE INVENTION

Indoline-2-carboxylic acids have heretofore been prepared by first forming the corresponding indole-2-carboxylic acid and then reducing the 2,3-double bond. The chief drawback in such preparations has been the lack of a satisfactory process for reducing the 2,3-double bond.

One of the methods of obtaining the indole-2-carboxylic acid to be reduced has been via the Reissert synthesis wherein o-nitrophenylpyruvic acid (III above where X is hydrogen) is reductively cyclized directly to the indoline-2-carboxylic acid using zinc and acetic acid or ferrous sulfate and ammonium hydroxide. See Weissberger, ed., *The Chemistry of Heterocyclic Compounds*, Vol. 25, part 1, pp. 396–399 (Wiley Interscience, New York, 1972).

Three methods are reported for reducing indole-2-carboxylic acid to indoline-2-carboxylic acid. Hudson and Robertson, Australian Journal of Chemistry, 20, 1935–41 (1967), first converted the acid to the amide and reduced the 2,3-double bond of the amide using phosphonium iodide/hydriodic acid. They then converted the resulting indoline-2-carboxamide to the desired indoline-2-carboxylic acid by hydrolysis. Y. Omote et al., Nippon Kagaku Zasshi, 87, 760 (1966), also reported an indirect reduction [See Stanton et al., Journal or Medicinal Chemistry, 26, 1267–77 at 1268 (1983)]. In this method the indole-2-carboxylic acid was first converted to the N-acetyl derivative which was reduced by hydrogenation at atmospheric pressure in the presence of platinum oxide. The resulting N-acetyl-indoline-2-carboxylic acid was then hydrolyzed to remove the acetyl group. Corey et al., Journal of the American Chemical Society, 92, 2476–2488, at 2480 (1970), directly reduced indole-2-carboxylic acid ethyl ester using excess dry hydrogen chloride gas and tin and absolute ethanol in a sealed bomb.

After obtaining indoline-2-carboxylic acid by one of these procedures, a resolution process would then have to be performed in order to obtain the desired chiral indoline-2-carboxylic acid. Here also one of the reported resolutions is indirect in that the indoline-2-carboxylic acid is first converted to its N-acetyl derivative. This derivative is resolved and the resolution product is converted back to the indoline-2-carboxylic acid. See Example 1 of U.S. Pat. No. 4,374,847 to N. Gruenfeld. A direct resolution of indoline-2-carboxylic acid using (+)-α-methylbenzylamine as a resolving agent is reported in Tetrahedron Letters, Vol. 23, No. 16, pp. 1677–80, at 1678 (April/May, 1982). However, no detail on yields is given in this report.

Applicants' process differs from all prior processes for the preparation of I or II in that either I or II, as desired, may be obtained as a single enantiomer without the concurrent formation of the opposing optical antipode.

The classical resolution process, as described above, which involves the generation of both optical enantiomers followed by separation of the desired from the undesired enantiomer, is less efficient because half of the material generated is lost in the form of the undesired enantiomer. The invention process is more efficient since it decreases the amount of material that is lost in the form of the undesired enantiomer.

The indoline-2-carboxylic acids of Formula I are useful as starting materials for the preparation of N-(3-mercapto-2-alkyl-1-oxopropyl)-indoline-2-carboxylic acids and N-(2-substituted-1-oxoalkyl)-indoline-2-carboxylic acids thereof which have antihypertensive and angiotensin converting enzyme (ACE) inhibitory properties. These antihypertensive agents and ACE inhibitors are disclosed in U.S. Pat. No. 4,303,583, issued on Dec. 1, 1981, to D. H. Kim and R. J. McCaully and in U.S. Pat. No. 4,350,633, issued on Sept. 21, 1982, also to D. H. Kim and R. J. McCaully. The indoline-2-carboxylic acids of structural Formulas I and II are useful as intermediates in further asymmetric syntheses of a variety of α-amino acids. (E. J. Corey, R. J. McCaully, H. S. Sachdev, J. Am. Chem. Soc., 1970, 92, 2476).

DETAILED DESCRIPTION OF THE INVENTION

Applicants' process for producing an asymmetric indoline-2-carboxylic acid of the structural Formula:

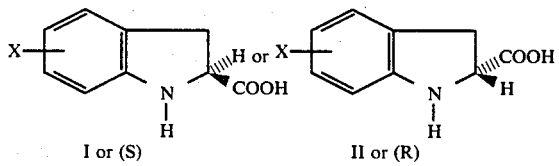

wherein X is hydrogen, bromine, chlorine, $C_{1-4}$ alkyl or $C_{1-4}$ alkoxy, comprises:

(a) assymetrically reducing an o-nitrophenylpyruvic acid of the Formula

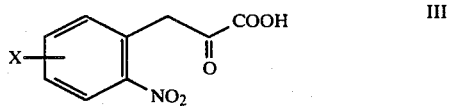

wherein X is as defined above, by contacting the acid III with a reducing complex formed from (R)-proline or (S)-proline, respectively, and sodium borohydride in an inert solvent to form, respectively, an (S) or (R)-α-hydroxy-2-nitrobenzenepropanoic acid of the formula

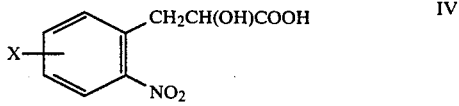

wherein X is as defined above;

(b) reacting, respectively, said (S) or (R)-α-hydroxy-2-nitrobenzenepropanoic acid IV wherein X is as defined above, with a Vilsmeier chlorinating reagent in which the chlorinating agent thereof is selected from a group consisting of thionyl chloride, oxalyl chloride, phosphorus oxychloride, phosphorus pentachloride and sulfuryl chloride and the amide thereof is selected from a group consisting of dimethylformamide, diethylformamide, dimethylacetamide and diethylacetamide, said reaction being run at temperatures of at least 20° C., in order to obtain, respectively, an (R) or (S)-α-chloro-2-nitrobenzenepropanoic acid of the formula:

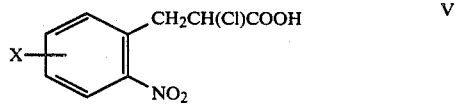

(c) reducing the nitro group of said (S) or (S)-α-chloro-2-nitrobenzenepropanoic acid (V) to an amino group; and (d) cyclizing the resulting (R) or (S) 2-amino-α-chlorobenzenepropanoic acid in aqueous base.

The process as illustrated for the synthesis of the (S)-enantiomer Ia (X=H) is shown above. A directly analogous scheme of reactions in which all chiral centers are inverted would be used if the corresponding R-enantiomer (II) is desired. The asymmetric reduction of o-nitrophenylpyruvic acid to (S)-α-hydroxy-2-nitrobenzenepropanoic acid utilizes a complex formed by contacting (R)-proline with sodium borohydride in an inert organic solvent. The complex is generated by stirring the ingredients at 0° to 50° C. but preferably at room temperature for 1 to 24 hours but preferably for 18 hours. To the resulting dispersion is added dropwise a solution of o-nitrophenylpyruvic acid in an inert ether solvent, such as tetrahydrofuran (THF), dioxane, or dimethoxyethane, in a molar ratio of complex to acid of 0.5 to 2.5 but preferably 0.85 to 1.0 and the reaction is allowed to proceed at 15° to 45° C. but preferably at 25° to 30° C. for one to ten days but preferably for 4 to 8 days. The solution was decanted from any insoluble residue and evaporated. The residues are digested with aqueous acid and extracted into an inert, immiscible organic solvent. Removal of the solvent affords primarily the (S)-α-hydroxy-2-nitrobenzenepropanoic acid which can be separated from the less soluble racemic compound by dissolution in an appropriate inert organic solvent such as ether or dichloromethane. Removal of the solvent affords sufficiently pure (S)-α-hydroxy-2-nitrobenzenepropanoic acid to be carried on to the next step. Alternatively, the intermediate can be recrystallized by treatment with an appropriate mixture of ethers and hydrocarbons or a single polar hydrocarbon solvent such as toluene.

In step B, the resulting (S)-α-hydroxy-2-nitrobenzenepropanoic acid (IV) is reacted with a Vilsmeier chlorinating reagent in order to form an (R)-α-chloro-2-nitrobenzenepropanoic acid (V) by replacement of the hydroxyl group with a chlorine atom. The Vilsmeier chlorinating reagent is formed from the combination of a chlorinating agent and an amide of the formula $R_2CONR_1R_1$, where $R_1$ and $R_2$ are preferably a methyl or ethyl group. A suitable chlorinating agent may be selected from thionyl chloride, oxalyl chloride, phosphorus oxychloride, phosphorus pentachloride, and sulfuryl chloride, with thionyl chloride being especially preferred. A suitable amide may be selected from N,N-dimethylformamide, N,N-diethylformamide, N,N-dimethylacetamide, or N,N-diethylacetamide, with N,N-dimethylformamide (DMF) being especially preferred. The Vilsmeier reagent may be formed separately and then added to the α-hydroxy-2-nitrobenzenepropanoic acid substrate, or the Vilsmeier reagent may be formed in situ, usually by combining the substrate and the amide first and then adding the chlorinating agent.

In order to ensure chlorination at both the hydroxy and acyl sites of the substrate, thereby avoiding intermolecular condensation, the amide portion of the Vilsmeier reagent is preferably present in 2–6 moles per mole of substrate. Good yields are obtained with 2–3 moles of amide per mole of substrate. For the same reason, the chlorinating agent should be present in at least 2 moles per mole of substrate. Preferably the chlorinating agent is present in excess of 4 moles per mole of substrate and may be present in up to 34 moles per mole of substrate. Such large excesses are used particularly when no inert solvent is used for the reaction.

Accordingly, the reaction of step B can be run without a solvent or with an inert organic solvent such as dichloromethane, dichloroethane, chloroform, methylene chloride or ethylene chloride. Dichloromethane is the preferred solvent. Additionally, temperatures above 20° C. are necessary when reaction B is in progress. Preferably, the reaction temperature is at least 25° C. and may vary up to about 50° C. depending upon the particular Vilsmeier reagent and solvent used. A prefered temperature range is 25°-35° C., and, at such temperatures, a reaction time of 12-24 hours is preferred. Conveniently, an overnight reaction of about 18 hours at room temperature of 25° C. is used. Evaporation of solvent and volatile components followed by quenching in ice affords the product which may be isolated by extraction into an inert immiscible organic solvent followed by evaporation. Purification of the α-chloroacid may be achieved by formation of a salt with an alicyclic or cyclic amine such as 2,6-dimethylpiperidine. The 2,6-dimethylpiperidine salt is particularly useful for the purification of (R)-α-chloro-2-nitrobenzene-propanoic acid and its separation from minor amounts of racemic product that may have carried through the asymmetric reduction step.

The (R)-α-chloro-2-nitrobenzenepropanoic acid (V) or its amine salt is next reduced in a basic medium to afford either the corresponding intermediate (R)-2-amino-α-chlorobenzenepropanoic acid (V) or the desired (S)-indoline-2-carboxylic acid (I). The reduction may be done catalytically in the presence of standard hydrogenation catalysts such as palladium on carbon in a hydrogen atmosphere, in which case the intermediate (V) is obtained. Alternatively, the reduction can be carried out with reducing agents that are compatible with a basic reaction medium, such as Raney nickel-hydrazine, in which case the desired (S)-indoline-2-carboxylic acid (I) is obtained directly.

In those instances in which the intermediate (VI) is generated and isolation is preferred, it is most convenient to isolate the compound as a salt formed with an alicyclic or cyclic amine. 2,6-Dimethylpiperidine is the preferred amine. Conversion of (VI) to the (S)-indoline-2-carboxylic acid (I) is achieved by contacting a dispersion of (VI) in a hydroxylic solvent with an alkaline metal hydroxide. Isolation of the product follows standard procedures.

As stated previously, if (R)-indoline-2-carboxylic acids (II) are desired, the same process is used except that all the chiral centers, including that of proline in step A, are reversed.

X, as defined herein, may also include fluorine and "halogen" refers to fluorine, chlorine and bromine.

EXAMPLE 1

(+)-α-Hydroxy-2-Nitrobenzenepropanoic Acid

D-(+)-proline (7.50 g., 65 mmol) and sodium borohydride (2.46 g., 65 mmol) were stirred gently together in dry tetrahydrofuran (400 ml.) for 18 hours. To the resulting suspension was added dropwise a solution of recrystallized o-nitrophenylpyruvic acid (14.17 g., 67.7 mmol) in dry THF (50 ml.). The resulting solution was stirred at room temperature for six days, decanted, and evaporated. The resulting gum was stirred with 10% aqueous HCl for five hours and the solution was extracted three times with 150 ml. portions of ether. The ether solution was dried (MgSO4) and evaporated to provide the crude product as a gummy solid. Residual solvent was removed by pumping with an oil pump overnight to give 12.05 g. (85%) of product $[\alpha]_D^{25}+49.94°$ (c 2.46, EtOH).

The aqueous solution from which the product had been extracted was stirred with 30 teaspoonfuls of Amberlite IR-120 (H+) ion exchange resin for three hours, poured into a column, and the resin was drained and washed with distilled water (1 L). The resin was then poured into a beaker and stirred for three hours with dilute ammonia (500 ml.). The resin was again poured into a column, drained and washed with water (500 ml.). The combined aqueous eluate was evaporated, and the solid residue was recrystallized from methanol-acetone to provide 5.62 g. (74.9%) of D-(+)-proline, m.p. 222°-224° C. $[\alpha]_D^{25}+83.99°$ (c 2.23, H2O).

EXAMPLE 2

(−)-α-Chloro-2-Nitrobenzenepropanoic Acid, 2,6-Dimethylpiperidine Salt

To magnetically stirred N,N-dimethylformamide (23 ml., 297.3 mmol) cooled in ice was slowly added dropwise thionyl chloride (139 ml., ca. 1.91 mol). A solution of (+)-α-hydroxy-2-nitrobenzenepropanoic acid [11.60 g., 54.9 mmol, $[\alpha]_D^{25}+49.94°$ (c, 2.465, 95% EtOH)], obtained from the chiral reduction of 2-nitro-α-oxobenzenepropanoic acid described in Example 1, in dichloromethane (133 ml.) was then added dropwise to the cold Vilsmeier reagent. The ice bath was removed and the solution, protected from moisture, was left at room temperature (25° C.) for 18 hours. The resulting yellow solution was evaporated to syrup. The syrup was dissolved in dichloromethane and the solution was poured cautiously onto stirred ice. The mixture was stirred for one hour during which time it warmed to room temperature. The organic phase was separated, washed (×3) with water and dried (MgSO4). Evaporation gave a syrup which was subjected to an oil pump vacuum for 0.5 hour. The syrup was dissolved in ether and 2,6-dimethylpiperidine was added to approximate neutrality (ca. pH 8 by pH paper). The crude titled compound (12.40 g., 66%) crystallized readily, m.p. 148°-153° C. Three crystallizations (with decolorization) from methanol-ether gave 6.01 g. (32% of pure product, m.p. 164°-167° C. dec., $[\alpha]_D^{25}-41.49°$ (c 1.005, 95% EtOH).

Analysis for: C9H8ClNO2.C7H15N. Calculated: C, 56.06; H, 6.76; Cl, 10.34; N, 8.17. Found: C, 56.17; H, 6.71; Cl, 10.17; N, 8.22.

EXAMPLE 3

(+)-α-Chloro-2-Aminobenzenepropanoic Acid, 2,6-Dimethylpiperidine Salt (−)-α-Chloro-2-nitrobenzenepropanoic acid, 2,6-dimethylpiperidine salt (2.06 g., 6.01 mmol) in anhydrous methanol (80 ml.) containing 2 drops (Pasteur pipette) of 2,6-dimethylpiperidine and 0.24 g. of 5% palladium on carbon was hydrogenated at ambient temperature and pressure until theoretical uptake had been achieved. The mixture was filtered through Celite, and the filtrate was evaporated. Coevaporation with cyclohexane gave a syrup which was subject briefly to an oil pump vacuum. Stirring with ether gave 1.45 g. (77%) of a white crystalline solid, m.p. 100°-101° C., $[\alpha]_D^{25}+16.00°$ (c 0.95, CHCl3).

Analysis for: C9H10ClNO2.C7H15N. Calculated: C, 61.43; H, 8.05; Cl, 11.33; N, 8.95. Found: C, 61.31; H, 7.82; Cl, 11.53; N, 8.92.

EXAMPLE 4

(S)-(+)-2,3-Dihydro-1H-Indole-2-Carboxylic Acid (+)-α-Chloro-2-aminobenzenepropanoic acid, 2,6-dimethylpiperidine salt (1.25 g., 4.00 mmol) was added to magnetically stirred N sodium hydroxide (4 ml.) under nitrogen. The solution was stirred under nitrogen overnight at room temperature. The pH was adjusted to a value between 2 and 3 (pH paper) with conc. hydrochloric acid while cooling in ice. The crystalline precipitate was collected and washed with several aliquots of ice cold water. The product was dried briefly under vacuum over phosphorous pentoxide and then stirred with ether. The product was dried over phosphorus pentoxide at 56° C. for several hours under oil pump vacuum to give 0.48 g. (74%) of the title compound, m.p. 155°–157° C., $[\alpha]_D^{25} = +36.09°$ (c 0.87, DMF).

Analysis for: $C_9H_9NO_2$. Calculated: C, 66.24; H, 5.56; N, 8.58. Found: C, 66.09; H, 5.67; N, 8.79.

IR, NMR and MS data were consistent with the structure.

EXAMPLE 5

(−)-α-Hydroxy-2-Nitrobenzenepropanoic Acid (±)-α-Hydroxy-2-nitrobenzenepropanoic acid (37.0 g., 0.175 mol) was added to a warm solution of (−)-quinine (28.4 g., 0.0875 mol) in ethyl acetate (350 ml.) and the mixture was swirled gently to effect solution. After standing for 36 hours the precipitated solid was filtered, washed consecutively with ethyl acetate and ether. After drying there was obtained the crude (−) acid (−) quinine salt (13.29 g.)—m.p. 165°–166° C. Recrystallization from ethyl acetate-ethanol (concentrated to about 300 ml.) afforded the pure salt (11.55 g.) m.p. 167°–168° C.

This salt was partitioned between ethyl acetate and a small volume of 10% aqueous HCl. The aqueous phase was extracted twice with ethyl acetate, and the combined ethyl acetate extracts were washed with brine. The solvent was removed under vacuum and the residue was dissolved in ether. The solution was filtered and again evaporated to dryness to provide 4.11 g. of the product, $[\alpha]_D^{25} -59.40°$ (c 2, EtOH).

EXAMPLE 6

(+)-α-Chloro-2-Nitrobenzenepropanoic Acid, 2,6-Dimethylpiperidine Salt From (−)-α-Hydroxy-2-Nitrobenzenepropanoic Acid That Was Obtained Via Resolution With Quinine To N,N-dimethylformamide (7.7 ml., 99.5 mmol) cooled in ice was slowly added thionyl chloride (46 ml., ca. 630 mmol) drop wise. (−)-α-Hydroxy-2-nitrobenzenepropanoic acid (3.83 g., 18.1 mmol), obtained in Example 5, was added in portions and the mixture was stirred at ice bath temperature for half an hour. The solution, protected from moisture, was left at room temperature (25° or more) overnight). The solution was evaporated to a syrup which was dissolved in dichloromethane. The dichloromethane solution was added cautiously to stirred ice, and the mixture was stirred for 1 hour, during which time it warmed to room temperature. The organic layer was washed thrice with water, dried over magnesium sulfate and evaporated to a syrup which was briefly subjected to an oil pump vacuum. The resulting syrup was dissolved in ether, and 2,6-dimethylpiperidine was added until the solution was slightly alkaline (pH paper). The crude titled product (4.87 g., 78% m.p. 145°–151° C.) crystallized readily. Fractional crystallization from methanol-ether gave 2.33 g. (37%) of the titled product [m.p. 164°–167° C., $[\alpha]_D^{25} +40.62°$ (c 0.965, 95% EtOH)] as the more insoluble component. (Racemic material was the more soluble component).

Analysis for: $C_9H_8ClNO_4.C_7H_{15}N$. Calculated: C, 56.06; H, 6.76; Cl, 10.34; N, 8.17. Found: C, 55.82; H, 6.82; Cl, 10.13; N, 8.02.

EXAMPLE 7

(−)-α-Hydroxy-2-Nitrobenzenepropanoic Acid

L-(−)-proline (7.50 g., 65.1 mmol) and sodium borohydride (2.46 g., 65.1 mmol) were stirred in tetrahydrofuran under nitrogen for sixteen hours. Recrystallized o-nitrophenylpyruvic acid (14.17 g., 76.5 mmol) in tetrahydrofuran (50 ml.) was added dropwise, and the resulting solution was stirred at room temperature for six days. The solvent was evaporated and the resulting gum was stirred with 10% aqueous HCl (200 ml.) for 4.5 hours. A small amount of solid was filtered to provide nearly racemic α-hydroxy-2-nitrobenzenepropanoic acid, 1.25 g., m.p. 98°–102° C., $[\alpha]_D^{25} -4.21°$ (c 2.045, EtOH).

The filtrate was extracted three times with ether (100 ml.), the combined extracts were dried (MgSO4) and evaporated (rotary evaporator and then oil pump overnight) to provide 10.90 g. (76%) of the title compound, m.p. 45°–50° C., $[\alpha]_D^{25} -56.85°$ (c 2.065, EtOH).

The aqueous solution from which the product had been extracted with ether was stirred with Amberlite IR-120 (30 teaspoonfuls) for 3 hours and the resin filtered and washed with water (1 L). The resin was then stirred with 50 ml. of concentrated NH4OH diluted to 500 ml. with water. The resin was filtered, washed with 500 ml. of water and the water removed under vacuum. The solid residue was dissolved in methanol (30 ml.), stirred and diluted by dropwise addition of acetone (300 ml.). The precipitated solid was filtered and dried to provide 3.75 g. (50%) L-(−)-proline, m.p. 228°–230° C. $[\alpha]_D^{25} -85.99°$ (c 2.22, H2O).

EXAMPLE 8

Purification of (−)-α-Hydroxy-2-Nitrobenzenepropanoic Acid 34.01 g. Crude (−)-α-hydroxy-2-nitrobenzenepropanoic acid, $[\alpha]_D^{25} -51.26°$ (c 1.67, 95% ethanol), was stirred magnetically in dichloromethane (100 ml.). The resulting solid was collected on a filter and washed with dichloromethane (50 ml.). The solid [4.22 g., m.p. 104°–108° C., $[\alpha]_D^{25} -9.56°$ (c 1.025, 95% ethanol)] was primarily racemic material. Purification of the filtrate (approximately 250 ml.) gave further crops [A, 1.07 g., m.p. 104°–107° C., $[\alpha]_D^{25} -19.33°$ (c 1.19, 95% ethanol) and B, 0.54 g., m.p. 104°–197° C., $[\alpha]_D^{25} -16.54°$ (c, 1.215, 95% ethanol)] of primarily racemic material. The dichloromethane solution was evaporated and the resulting syrup subjected to an oil pump vacuum. The syrup solidified to give 26.50 g. of a yellow waxy solid, $[\alpha]_D^{25} -63.04°$ (c 0.955, 95% ethanol).

Analysis for: $C_9H_9NO_5$. Calculated: C, 51.19; H, 4.30; N, 6.63. Found: C, 51.47; H, 4.61; N, 6.53.

The above material (5.0 g.) was stirred magnetically with boiling ether (1 l.) and the mixture filtered through celite. The filtrate was boiled down to approximately 100 ml. and a small quantity of solid was removed by a further filtration. The resulting clear solution was boiled down to approximately 50 ml. and poured into magnetically stirred pentane (400 ml.). Scratching and stirring gave 3.06 g. of a yellow solid, m.p. 63°–67° C., $[\alpha]_D^{25} - 68.79°$ (c 0.99, 95% ethanol).

Analysis for: $C_9H_9NO_5$. Calculated: C, 51.19; H, 4.30; N, 6.63. Found: C, 51.31; H, 4.34; N, 6.64.

The solid (2.98 g.) was dissolved in ether (25 ml.) and the solution was decolorized and evaporated to smaller volume. Toluene was added and product [0.62 g., m.p. 89°–91°, $[\alpha_D^{25} - 75.19°$ (c 1.31, 95% ethanol)] was allowed to crystallize slowly at room temperature in a flask open to the atmosphere.

Analysis for: $C_9H_9NO_5$. Calculated: C, 51.19; H, 4.30; N, 6.63. Found: C, 51.54; H, 4.25; N, 6.94.

Recrystallization of 0.5 g. of the material from ether-toluene gave 0.35 g. of product, m.p. 88°–90°, $[\alpha]_D^{25} - 77.77°$ (c 1.705, 95% ethanol).

Analysis for: $C_9H_9NO_5$. Calculated: C, 51.19; H, 4.30; N, 6.63. Found: C, 51.24; H, 4.22; N, 6.73.

IR, $^1$HNMR and mass spectral data were consistent for the above structure.

EXAMPLE 9

(+)-α-Chloro-2-Nitrobenzenepropanoic Acid, 2,6-Dimethylpiperidine Salt

To magnetically stirred N,N-dimethylformamide (21 ml., 271.4 mmol.) cooled in ice was slowly added thionyl chloride (126 ml., ca. 1.73 mol) dropwise. A solution of 10.50 g. (49.7 mmol) of (−)-α-hydroxy-2-nitrobenzenepropanoic acid, obtained from the chiral reduction in Example 7, in dichloromethane (120 ml.) was added dropwise to the cold Vilsmeier reagent. The ice bath was removed and the solution, protected from moisture, was left at room temperature (25° C.) for 18.5 hours. The resulting yellow solution was evaporated to a syrup. The syrup was dissolved in dichloromethane and the solution was poured cautiously onto stirred ice. The mixture was stirred for one hour during which time it warmed to room temperature. The organic phase was separated, washed (×4) with water and dried (MgSO$_4$). Evaporation gave a syrup which was subjected to an oil pump vacuum for half an hour. The syrup was dissolved in ether and 2,6-dimethylpiperidine was added to approximate neutrality (ca. pH 8 by pH paper). The crude titled compound (12.46 g., 73%, m.p. 148°–156° C. dec.) crystallized readily. Recrystallization from methanol-ether gave 7.74 g. (crop A) of product (m.p. 163°–166° C. dec.).

The mother liquor yielded further crops (B, 2.97 g., m.p. 140°–152° C. and C, 0.47 g., m.p. 139°–141° C.). Three crystallizations of crop B from methanol-ether gave 0.60 g., m.p. 164°–167° C. dec. Recombination of that material with the major crop A followed by recrystallization gave 7.21 g. (42%) of pure product, m.p. 164°–167° dec. $[\alpha]_D^{25} + 41.03$ (c 1.07, 95% EtOH).

Analysis for: $C_9H_8ClNO_2.C_7H_{15}N$. Calculated: C, 56.06; H, 6.76; Cl, 10.34; N, 8.17. Found: C, 56.05; H, 6.73; Cl, 10.35; N, 8.14.

EXAMPLE 10

(+)-α-Chloro-2-Nitrobenzenepropanoic Acid, 2,6-Dimethylpiperidine Salt

To magnetically stirred N,N-dimethylformamide (3 ml.) 38.8 mmol) cooled in ice was added slowly dropwise thionyl chloride (4.5 ml., 61.7 mmol). (−)-α-Hydroxy-2-nitrobenzenepropanoic acid (3.01 g., 14.2 mmoles), $[\alpha]_D^{25} - 63.04°$ (c 0.955, 95% ethanol), in dichloromethane (35 ml.) was added to the cold vilsmeier reagent, and the resulting solution, protected from moisture, was left at room temperture (25° C.) overnight. The solution was added to stirred ice, and the mixture was stirred for 1 hour, during which time it warmed to room temperature. The dichloromethane solution was separated and washed twice with water and dried (MgSO$_4$). Evaporation gave a syrup which was subjected to an oil pump vacuum for 0.5 hour. The syrup was dissolved in ether, and 2,6-dimethylpiperidine was added to approximate neutrality (pH 8 with pH paper). The crude titled product [2.95 g. (60%), m.p. 154°–158° C. dec.] crystallized readily. Fractional crystallization (methanol-ether) with decolorization (Nuchar C-190N) gave 1.59 g. (33%) of titled product, m.p. 164°–167° dec., $[\alpha]_D^{24} + 41.46$ (c 1.275, 95% ethanol).

Analysis for: $C_9H_8ClNO_4.C_7H_{15}N$. Calculated: C, 56.06; H, 6.76; Cl, 10.34; N, 8.17. Found: C, 56.42; H, 6.85; Cl, 10.25; N, 8.14.

IR, $^1$HNMR and mass spectral data were consistent with the above structure.

EXAMPLE 11

(+)-α-Chloro-2-Nitrobenzenepropanoic Acid 2,6-Dimethylpiperidine Salt

To magnetically stirred N,N-dimethylformamide (3 mL) cooled in ice was added slowly dropwise thionyl chloride (4.5 ml., 61.7 mmol) and the resulting cold Vilsmeier reagent was diluted with dichloromethane (30 ml.). (−)-α-Hydroxy-2-nitrobenzenepropanoic acid [3.00 g., 14.2 mmol, $[\alpha]_D^{25} - 63.04°$ (c 0.955, 95% ethanol)] in dichloromethane (70 ml.) was added. The resulting solution, protected from moisture, was left at room temperature (25° overnight. The solution was added to stirred ice and the mixture was stirred for 1 hour, during which time it warmed to room temperature. The dichloromethane solution was separated and washed thrice with water and dried (MgSO$_4$). Evaporation gave a syrup which was subjected to an oil pump vacuum for 1.5 hours. The syrup was dissolved in ether and 2,6-dimethylpiperidine was added to approximate neutrality (pH 9 with pH paper). The crude titled product [2.98 g. (61%), m.p. 155°–158° C. dec.] crystallized readily. Two crystallizations (methanol-ether) with decolorization (Nuchar C-190N) gave 1.91 g. (39%) of pure product; m.p. 164°–167° C. dec., $[\alpha]_D^{25} + 42.11°$ (c 1.09, 95% ethanol).

Analysis for: $C_9H_8ClNO_4. C_7H_{15}N$. Calculated: C, 56.06; H, 6.76; Cl, 10.34; N, 8.17. Found: C, 56.12; H, 6.71; Cl, 10.48; N, 8.18.

IR, $^1$HNMR and mass spectral data were consistent with the above structure.

EXAMPLE 12

(−)-α-Chloro-2-Aminobenzenepropanoic Acid, 2,6-Dimethylpiperidine Salt (+)-α-Chloro-b 2-nitrobenzenepropanoic acid, 2,6-dimethylpiperidine salt (2.06 g., 6.01 mmol) in anhydrous methanol (80 ml.) containing 2 drops (Pasteur pipette) of 2,6-dimethylpiperidine and 0.24 g. of 5% palladium on carbon was hydrogenated at ambient temperature and pressure until the theoretical uptake had been achieved. The mixture was filtered through celite and the filtrate was evaporated. Coevaporation with cyclohexane gave a syrup which was subjected briefly to an oil pump vacuum. Stirring with ether containing a small proportion of cyclohexane gave 1.45 g. (77%) of product as a white crystalline solid, m.p. 101°–103° C., $[\alpha]_D^{25} -15.73°$ (c 1.03, chloroform).

Analysis for: $C_9H_{10}ClNO_2 \cdot C_7H_{15}N$. Calculated: C, 61.43; H, 8.05; Cl, 11.33; N, 8.95. Found: C, 60.89; H, 8.17; Cl, 11.60; N, 8.62.

EXAMPLE 13

(R)-(−)-2,3-Dihydro-1H-Indole-2-Carboxylic Acid (−)-α-Chloro-2-aminobenzenepropanoic acid 2,6-dimethylpiperidine salt (1.25 g., 4.00 mmol) was added to magnetically stirred N NaOH (4 ml.) under nitrogen. The solution was stirred under nitrogen overnight at room temperature. The pH was adjusted to a value between 2 and 3 with concentrated hydrochloric acid and the mixture cooled in ice. The resulting crystals were collected and washed with several aliquots of ice cold water. The product was dried briefly under vacuum over phsophorus pentoxide and then stirred with ether. The product was collected and dried over phosphorus pentoxide at 56° for several hours under oil pump vacuum to give 0.43 g. (65%) of product, m.p. 151°–156° C., $[\alpha]_D^{25} -38.53°$ (c 0.95, DMF).

Analysis for: $C_9H_9NO_2 \cdot 0.1H_2O$. Calculated: C, 65.52; H, 5.62; N, 8.49. Found: C, 65.64; H, 5.64; N, 8.53.

What is claimed is:

1. An asymmetric α-chloro-2-aminobenzenepropanoic acid of the formula:

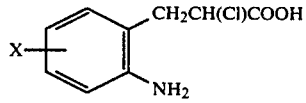

wherein X is hydrogen, bromine, chlorine, $C_{1-4}$ alkyl or $C_{1-4}$ alkoxy.

2. A compound according to claim 1 which is (R)-α-chloro-2-aminobenzenepropanoic acid.

3. A compound according to claim 1 which is (S)-α-chloro-2-aminobenzenepropanoic acid.

* * * * *